(12) United States Patent
Nagel et al.

(10) Patent No.: US 9,364,614 B2
(45) Date of Patent: Jun. 14, 2016

(54) DRUG DELIVERY DEVICE

(71) Applicant: SANOFI-AVENTIS DEUTSCHLAND GMBH, Frankfurt am Main (DE)

(72) Inventors: Thomas Nagel, Tharandt (DE); Rene Richter, Tharandt (DE); Robert Witt, Dresden (DE); Richard Guenther, Dresden (DE); Martin Graefe, Pirna (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/405,991

(22) PCT Filed: Jun. 25, 2013

(86) PCT No.: PCT/EP2013/063238
§ 371 (c)(1),
(2) Date: Dec. 5, 2014

(87) PCT Pub. No.: WO2014/001310
PCT Pub. Date: Jan. 3, 2014

(65) Prior Publication Data
US 2015/0126940 A1 May 7, 2015

(30) Foreign Application Priority Data
Jun. 27, 2012 (EP) .................................... 12173961

(51) Int. Cl.
A61M 5/24 (2006.01)
A61M 5/315 (2006.01)
A61M 5/30 (2006.01)

(52) U.S. Cl.
CPC . A61M 5/24 (2013.01); A61M 5/30 (2013.01); A61M 5/31511 (2013.01)

(58) Field of Classification Search
CPC ..................... A61M 5/14216; A61M 5/31511; A61M 5/1452; A61M 5/20; A61M 1/0068; A61M 1/1081; F04B 53/1082; Y10S 128/01
See application file for complete search history.

(56) References Cited

U.S. PATENT DOCUMENTS 3,964,481 A * 6/1976 Gourlandt et al. ............. 604/152
4,108,177 A * 8/1978 Pistor ............................ 604/155
(Continued)

FOREIGN PATENT DOCUMENTS

CN 201875042 6/2011
CN 102162499 8/2011

OTHER PUBLICATIONS

International Search Report for Int. App. No. PCT/EP2013/063238, completed Aug. 2, 2013.

Primary Examiner — Imani Hayman
Assistant Examiner — William Carpenter
(74) Attorney, Agent, or Firm — McDonnell Boehnen Hulbert & Berghoff LLP

(57) ABSTRACT

The invention relates to a drug delivery device, comprising:
a case for retaining drug container, the drug container defining a cavity for containing a drug, wherein a stopper is slidably disposed within the container so as to displace the drug through a discharge nozzle on translation in a distal direction,
an inner magnet disposable within the drug container for abutting the stopper,
at least one outer magnet disposed within the case coaxially with the container and slidable in an axial direction,
a trigger arrangement for advancing the outer magnet in a distal direction on actuation,
wherein the outer magnet and inner magnet are arranged for magnetically interacting through the drug container wall such the outer magnet advances the inner magnet on trigger actuation.

13 Claims, 1 Drawing Sheet

(56) References Cited

U.S. PATENT DOCUMENTS

| | | | |
|---|---|---|---|
| 4,610,658 A * | 9/1986 | Buchwald et al. | 604/9 |
| 5,139,484 A * | 8/1992 | Hazon et al. | 604/154 |
| 7,201,746 B2 * | 4/2007 | Olsen | 604/891.1 |
| 7,255,684 B2 * | 8/2007 | Zubry | 604/131 |
| 7,455,658 B2 * | 11/2008 | Wang | 604/85 |
| 7,516,873 B2 * | 4/2009 | Wang | 222/333 |
| 8,348,106 B2 * | 1/2013 | Wang | 222/333 |
| 2002/0022807 A1 * | 2/2002 | Duchon et al. | 604/228 |
| 2005/0277887 A1 * | 12/2005 | Douglas et al. | 604/173 |
| 2006/0030816 A1 * | 2/2006 | Zubry | 604/131 |
| 2007/0066939 A1 * | 3/2007 | Krulevitch et al. | 604/152 |
| 2007/0093751 A1 * | 4/2007 | Harttig | 604/131 |
| 2010/0286613 A1 * | 11/2010 | Ring | 604/152 |
| 2011/0301566 A1 * | 12/2011 | Schaefer | 604/500 |

* cited by examiner

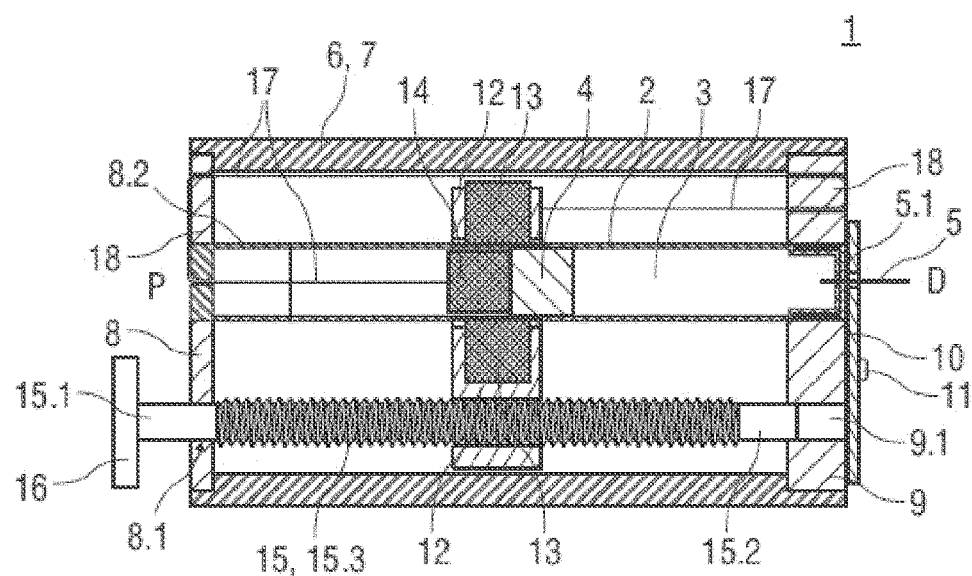

DRUG DELIVERY DEVICE

CROSS REFERENCE TO RELATED APPLICATIONS

The present application is a U.S. National Phase Application pursuant to 35 U.S.C. §371 of International Application No. PCT/EP2013/063238 filed Jun. 25, 2013, which claims priority to European Patent Application No. 12173961.9 filed Jun. 27, 2012. The entire disclosure contents of these applications are herewith incorporated by reference into the present application.

TECHNICAL FIELD

The invention relates to a drug delivery device.

BACKGROUND

Conventional drug delivery devices comprise a container defining a cavity within for retaining a drug, a nozzle, e.g. an injection needle arranged at a distal end of the container, wherein the nozzle is in fluid communication with the cavity, and a stopper with a plunger disposed in the container for displacing the drug.

US 2006/030816 A1 discloses a method and apparatus for the storage and transfer of medical material. In one aspect of the invention a syringe having rodless piston magnetically couples to an actuator that is positioned along the syringe independent of the rodless piston. Another aspect contemplates using medical material in a cartridge that is used to store like an ampoule and transfer like a syringe.

SUMMARY

It is an object of the present invention to provide an improved drug delivery device.

The object is achieved by a drug delivery device according to claim 1.

Preferred embodiments of the invention are given in the dependent claims.

A drug delivery device according to the invention comprises:
- a case for retaining a drug container, the drug container defining a cavity for containing a drug, wherein a stopper is slidably disposed within the container so as to displace the drug through a discharge nozzle on translation in a distal direction,
- an inner magnet disposable within the drug container for abutting the stopper,
- at least one outer magnet disposed within the case coaxially with the container and slidable in an axial direction,
- a trigger arrangement for advancing the outer magnet in a distal direction on actuation,
wherein the outer magnet and inner magnet are arranged for magnetically interacting through the drug container wall such the outer magnet advances the inner magnet on trigger actuation.

Conventional art pen injectors have a piston rod for displacing the stopper within the drug container. In order to fully empty the drug container the piston rod must have approximately the length of the drug container. An overall length of the pen injector is therefore about twice the length of the piston rod. By contrast, in the drug delivery device according to the invention, the force for moving the stopper is not applied inside the drug container but from outside through the container wall by the interacting outer and inner magnet. Hence, a conventional piston rod is not required thus allowing for nearly halving the overall length of the drug delivery device, which is thus more compact.

In an exemplary embodiment, a cord with a low flexibility (with respect to its length) is arranged between a proximal face of the inner magnet and the outer magnet so as to define their relative axial position. The cord is preferably tear-resistant and strained by the force between the magnets.

In an exemplary embodiment the cord comprises steel and/or polyethylene and/or aramid fibres.

In an exemplary embodiment the cord runs from the inner magnet in the proximal direction through a deviating point in a proximal rear cover of the case, then back in the distal direction and through another deviating point in a distal front cover and again in the proximal direction to the outer magnet. This allows for a compact arrangement.

In an exemplary embodiment a length of the cord is set so as to keep the inner magnet and the outer magnet away from a rest position of the inner magnet with respect to the outer magnet, e.g. a position in which the attraction between the magnets would cause no further movement.

This offset from the rest position keeps the cord tight. Due to the low flexibility of the cord and the magnetic interaction between the magnets the relative axial offset between the magnets is held constant. Thus, when the outer magnet is moved by a certain distance the inner magnet moves by the same distance thus allowing for high dose accuracy.

In an exemplary embodiment the inner magnet and outer magnet are polarized and axially offset by the cord so as to attract each other. However, movement of the magnets is only allowed on actuation of a trigger. The outer magnet therefore drags the inner magnet when being moved on trigger actuation.

In another exemplary embodiment the inner magnet and outer magnet are polarized and axially offset by the cord so as to repel each other. The outer magnet therefore pushes the inner magnet when being translated on trigger actuation.

In an exemplary embodiment a rear cover of the case comprises a container socket arranged to receive the inner magnet, wherein the container socket is axially aligned with the drug container. The container socket serves for defining the position of the inner magnet prior to insertion of a new drug container.

In an exemplary embodiment a magnet retainer is arranged in the case for retaining the outer magnet. The magnet retainer facilitates interaction with the trigger arrangement and the cord and improves longitudinal guiding of the outer magnet.

In an exemplary embodiment the outer magnet is arranged as a ring magnet. Likewise, a number of outer magnets may be coaxially arranged around the drug container.

In an exemplary embodiment the inner magnet is arranged as a cylindrical magnet.

In an exemplary embodiment the trigger arrangement comprises a threaded bolt threaded to the outer magnet or the magnet retainer, wherein the threaded bolt is axially translatable within case by a limited distance. A dose to be delivered by the drug delivery device may be set by rotating the threaded bolt which consequently moves in the proximal direction with respect to the outer magnet depending on the number of rotations and/or angle of rotation and the pitch of the threaded bolt. Thus, the distance, by which the threaded bolt can be depressed and hence the distance, by which the stopper is shifted on depression of the threaded bolt is varied. Stopper displacement is proportional to the delivered dose.

In an exemplary embodiment a mechanical stop is arranged between the threaded bolt and the case for limiting relative axial translation. The limit may be set by a threaded section of the threaded bolt having a greater diameter than a non-threaded section or by a respective collar on the threaded bolt with an increased diameter so that the part with the smaller diameter may pass through an opening in the case but the greater diameter part may not.

In an exemplary embodiment a dosing handle is attached to the threaded bolt and extends proximally from the rear cover so as to allow a user to grab, rotate and press it. The dosing handle may also serve as the limit for moving the threaded bolt. A scale marking may be provided on the case or on the dosing handle for relating the angle of rotation to the dose to be delivered.

In an exemplary embodiment the discharge nozzle may be arranged as an injection needle or a jet nozzle.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by $\alpha$, $\delta$, $\epsilon$, $\gamma$, and $\mu$. The type of heavy chain present defines the isotype of antibody; these chains are found in IgA, IgD, IgE, IgG, and IgM antibodies, respectively.

Distinct heavy chains differ in size and composition; $\alpha$ and $\gamma$ contain approximately 450 amino acids and $\delta$ approximately 500 amino acids, while $\mu$ and $\epsilon$ have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains $\gamma$, $\alpha$ and $\delta$ have a constant region composed of three tandem Ig domains, and a hinge region for added flexibility; heavy chains $\mu$ and $\epsilon$ have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by $\lambda$ and $\kappa$. A light chain has two successive domains: one constant domain (CL) and one variable domain (VL). The approximate length of a light chain is 211 to 217 amino acids. Each antibody contains two light chains that are always identical; only one type of light chain, $\kappa$ or $\lambda$, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1 is a schematic longitudinal section of a drug delivery device.

DETAILED DESCRIPTION

FIG. 1 is a schematic longitudinal section of a drug delivery device 1. The drug delivery device 1 comprises a drug container 2, e.g. a syringe defining a cavity 3 for containing a drug. The cavity is proximally delimited by a stopper 4 slidably arranged within the container 2 so as to displace the drug from the cavity through a discharge nozzle 5 arranged distally on the container 2. The discharge nozzle 5 may be arranged as an injection needle or a jet nozzle. The discharge nozzle 5 may be attached to the drug container 2 by a nozzle connector 5.1 such as a needle hub.

The drug container 2 is retained within a case 6. The case 6 comprises a cylinder 7 whose end faces are closed by a rear cover 8 and a front cover 9. The front cover 9 has an aperture for allowing the discharge nozzle 5 to extend from the case and/or to allow insertion of the drug container 2 into the case 6. A front retaining plate 10 is distally attached to the front cover 9 reducing the width of the aperture for fixing the drug container 2 in its axial position once it is inserted. The front retaining plate 10 may be attached to the front cover by at least one screw 11.

The rear cover 8 comprises a container socket 8.2 having essentially the same internal diameter as the outer diameter of the drug container 2. The container socket 8.2 is axially aligned with the drug container 2. In order to maintain alignments the rear cover 8 and front cover 9 may be rotationally fixed to the cylinder 7, e.g. by gluing or screwing.

Inside the case 6 a magnet retainer 12 is arranged over the drug container 2 and movable in an axial direction. The magnet retainer 12 holds at least one outer magnet 13 which may be arranged as a ring magnet. An inner magnet 14 for interacting with the outer magnet 13 is arranged within the drug container 2 proximally from the stopper 4. The inner magnet 14 is preferably cylindrical.

A threaded bolt 15 is arranged in parallel with the drug container 2 within the case 6. The threaded bolt 15 engages the magnet retainer 12 which has a corresponding screw thread such that the magnet retainer 12 is translated in the axial direction on rotation of the threaded bolt 15. A dosing handle 16 is attached to the threaded bolt 15 and extends proximally from the rear cover 8 so as to allow a user to grab, rotate and press it.

The threaded bolt 15 has two non-threaded sections 15.1, 15.2 at its distal and proximal ends and a threaded section 15.3 in between, wherein the non-threaded sections 15.1, 15.2 are axially guided in respective guiding bores 8.1, 9.1 within the rear cover 8 and front cover 9 so as to allow some axial translation of the threaded bolt 15 relative to the case 6, which may be limited by the threaded section 15.3 of the threaded bolt 15 having a greater diameter than the non-threaded sections 15.1, 15.2 or by a respective collar on the threaded bolt 15 with an increased diameter or by the dosing handle 16 abutting the rear cover 8.

A tear-resistant, tightened cord 17 with low or no flexibility, e.g. comprising steel and/or polyethylene and/or aramid fibres connects the proximal face of the inner magnet 14 with the distal face of the magnet retainer 12, wherein the cord 17 runs from the inner magnet 14 in the proximal direction P through the container socket 8.2 into a deviating point 18 in the rear cover 8, then back in the distal direction D near the wall of the cylinder 7 and through another deviating point 18 in the front cover 9 and eventually again in the proximal direction P to the magnet retainer 12.

The inner magnet 14 is polarized with respect to the outer magnet 13 such that they attract each other and tend to arrive in a relative rest position.

However, the length of the cord 17 is set so as to keep the inner magnet 14 and the outer magnet 13 axially offset, i.e. a small distance away from the rest position of the inner magnet 14 with respect to the outer magnet 13. This offset keeps the cord 17 tight. Due to the low flexibility of the cord 17 and the magnetic attraction between the magnets 13, 14 the relative axial offset between the magnets 13, 14 is held constant. Thus, when the outer magnet 13 is moved by a certain distance the inner magnet 14 moves by the same distance thus allowing for high dose accuracy.

A dose to be delivered by the drug delivery device 1 may be set by rotating the dosing handle 16 and hence the threaded bolt 15 which consequently moves in the proximal direction P depending on the number of rotations and/or angle of rotation and the pitch of the threaded section 15.3. Thus, the distance, by which the corded bolt 15 can be depressed and hence the distance, by which the stopper 4 is shifted on depression of the dosing handle 16, is varied. The stopper displacement is proportional to the delivered dose.

In the illustrated embodiment the threaded bolt 15 comprises a right handed screw thread. Hence, when looking onto the dosing handle 16 from the distal end the dose is set by rotating the dosing handle 16 counter-clockwise. It goes without saying that the corded bolt 15 could likewise comprise a left handed screw cord such that the dose could be set by clockwise rotation.

After setting the intended dose the user may find a suitable injection site and place the distal end of the drug delivery device 1 against the injection site thereby inserting the injection needle 5 into the injection site, if applicable. The user may then depress the dosing handle 16 thereby advancing the threaded bolt 15 until the displacement of the threaded bolt 15 is limited as described above.

Advancing the threaded bolt 15 also advances the magnet retainer 12 with the outer magnet 13. Due to the magnetic attraction the inner magnet 14 is also dragged in the distal direction D and thus displaces the stopper 4 thereby delivering the set dose through the discharge nozzle 5.

The operations of dose setting and delivery may be repeated until the drug container 2 is empty.

Once the drug container 2 is empty it may be replaced by rotating the dosing handle 16 in the clockwise sense until the inner magnet 14 is within the container socket 8.2. The front retaining plate 10 may then be loosened, the drug container 2 removed, a new one inserted and the retaining plate 10 re-attached.

The cylinder 7 of the case 6 may likewise be integrally shaped with the rear cover 8 and/or the front cover 9.

The invention claimed is:

1. Drug delivery device, comprising:
    a drug container, the drug container defining a cavity for containing a drug, wherein a stopper is slidably disposed within the container so as to displace the drug through a discharge nozzle on translation in a distal direction, a case for retaining the drug container, an inner magnet disposable within the drug container for abutting the stopper, at least one outer magnet disposed within the case coaxially with the container and slidable in an axial direction, a trigger arrangement for advancing the outer magnet in a distal direction on actuation, wherein the outer magnet and the inner magnet are arranged for magnetically interacting through the drug container wall such the outer magnet advances the inner magnet on trigger actuation, characterized in that a cord with a low flexibility is arranged between a proximal face of the inner magnet and the outer magnet so as to define their relative axial position, and wherein the cord runs from the inner magnet in the proximal direction through a deviating point in a proximal rear cover of the case, then back in the distal direction and through another deviating point in a distal front cover and again in the proximal direction to the outer magnet.

2. Drug delivery device according to claim 1, characterized in that the cord comprises steel and/or polyethylene and/or aramid fibres.

3. Drug delivery device according to claim 1, characterized in that a length of the cord is set so as to keep the inner magnet and the outer magnet away from a rest position of the inner magnet with respect to the outer magnet.

4. Drug delivery device according to claim 1, characterized in that the inner magnet and outer magnet are polarized and axially offset by the cord so as to attract each other.

5. Drug delivery device according to claim 1, characterized in that the inner magnet and outer magnet are polarized and axially offset by the cord so as to repel each other.

6. Drug delivery device according to claim 1, characterized in that a rear cover of the case comprises a container socket arranged to receive the inner magnet, wherein the container socket is axially aligned with the drug container.

7. Drug delivery device according to claim 1, characterized in that a magnet retainer is arranged in the case for retaining the outer magnet.

8. Drug delivery device according to claim 1, characterized in that the outer magnet is arranged as a ring magnet.

9. Drug delivery device according to claim 1, characterized in that the inner magnet is arranged as a cylindrical magnet.

10. Drug delivery device according to claim 1, characterized in that the trigger arrangement comprises a threaded bolt threaded to the outer magnet or a magnet retainer, wherein the threaded bolt is axially translatable within case by a limited distance.

11. Drug delivery device according to claim 10, characterized in that a mechanical stop is arranged between the threaded bolt and the case for limiting relative axial translation.

12. Drug delivery device according to claim 10, characterized in that a dosing handle is attached to the threaded bolt and extends proximally from the rear cover so as to allow a user to grab, rotate and press it.

13. Drug delivery device according to claim 1, characterized in that the discharge nozzle is arranged as an injection needle or a jet nozzle.

\* \* \* \* \*